United States Patent
Fishman et al.

(10) Patent No.: US 7,825,102 B2
(45) Date of Patent: Nov. 2, 2010

(54) TREATMENT OF DRY EYE CONDITIONS

(75) Inventors: Pnina Fishman, Herzliya (IL); Tatiana Reitblat, Petach Tikva (IL); Ilan Cohn, Herzliya (IL)

(73) Assignee: Can-Fite Biopharma Ltd., Petach Tikva (IL)

( * ) Notice: Subject to any disclaimer, the term of this patent is extended or adjusted under 35 U.S.C. 154(b) by 0 days.

(21) Appl. No.: 11/604,905

(22) Filed: Nov. 28, 2006

(65) Prior Publication Data

US 2007/0099865 A1    May 3, 2007

Related U.S. Application Data

(63) Continuation-in-part of application No. PCT/IL2006/000130, filed on Feb. 1, 2006, and a continuation-in-part of application No. PCT/IL2005/000762, filed on Jul. 18, 2005.

(60) Provisional application No. 60/762,506, filed on Jan. 27, 2006, provisional application No. 60/591,628, filed on Jul. 28, 2004.

(51) Int. Cl.
 *A61K 31/70* (2006.01)
(52) U.S. Cl. .................................. 514/46; 514/912
(58) Field of Classification Search .................. 514/46, 514/912
See application file for complete search history.

(56) References Cited

U.S. PATENT DOCUMENTS

| | | | |
|---|---|---|---|
| 5,573,772 A | 11/1996 | Downey et al. |
| 5,688,774 A | 11/1997 | Jacobson et al. |
| 5,773,423 A | 6/1998 | Jacobson et al. |
| 5,780,481 A | 7/1998 | Jacobson et al. |

FOREIGN PATENT DOCUMENTS

| | | |
|---|---|---|
| WO | 99/06053 A1 | 2/1999 |
| WO | 01/19360 A2 | 3/2001 |
| WO | 02/083152 A1 | 10/2002 |
| WO | 2004/029025 A2 | 4/2004 |
| WO | 2006/011130 A1 | 2/2006 |

OTHER PUBLICATIONS

Holly, F.J.,"Tear Film Physiology," *International Ophthalmology Clinics*, vol. 27, No. 1, pp. 2-6, (1987).

*Primary Examiner*—Zohreh A Fay
(74) *Attorney, Agent, or Firm*—The Nath Law Group; Susanne M. Hopkins; Ari G. Zytcer

(57) ABSTRACT

The present invention provides a method for treating dry eye condition in an individual comprising administrating to said individual an amount of $A_3$ adenosine receptor ($A_3AR$) agonist, the amount being effective to ameliorate symptoms of dry eye in the individual. In accordance with one embodiment, the dry eye condition is manifested by one or more ophthalmologic clinical symptoms selected from foreign body sensation, burning, itching, irritation, redness, eye pain, blurred vision, degraded vision and excessive tearing. A preferred $A_3RAg$ in accordance with the invention is $N^6$-(3-iodobenzyl)-adenosine-5'-N-methyluronamide (IB-MECA).

15 Claims, No Drawings

TREATMENT OF DRY EYE CONDITIONS

This is a Continuation-In-Part of International PCT Application No. PCT/IL2005/000762 with international filing date of 18 Jul. 2005 and International PCT Application No. PCT/IL2006/000130 (not yet published) and claims benefit from U.S. Provisional Application 60/591,628 filed 28 Jul. 2004, the contents of which are hereby incorporated by reference in their entirety.

FIELD OF THE INVENTION

The invention relates to compounds and methods useful in the treatment of dry eye conditions.

BACKGROUND OF THE INVENTION

As noted by Sullivan in U.S. Pat. No. 5,620,921 (Sullivan '921), "The preocular tear film plays an important role in the maintenance of corneal integrity, the protection against infection and the preservation of visual acuity." A healthy tear film preserves the optical clarity and refractive power, provides lubrication of the ocular surface and protection from environmental and infectious attacks. Sullivan '921 further notes that "These functions, in turn, are critically dependent upon the stability, tonicity and/or composition of the tear film structure. Healthy tears contain a complex mixture of proteins such as antimicrobial proteins (lysozyme, lactoferrin) and growth factors and inflammation suppressors, mucin which provides viscosity and stability of the tear and electrolytes for proper osmolarity. Alteration, deficiency or absence of the tear film may lead to undesired dryness of the corneal epithelium, ulceration and perforation of the cornea, an increased incidence of infectious disease, and ultimately, severe visual impairment and blindness." (See Sullivan '921 at col. 1, lines 19-30.)

The condition of dry eye is often referred to as a syndrome, or a disease; and it is likewise known by a variety of terms. Keratoconjunctivitis sicca (KCS), or more commonly keratitis sicca, refers to any eye with some degree of dryness.

In dry eye the eye becomes dry either because there is abnormally high rate of evaporation of tears or because there is not enough tears being produced. The contents of the tear in an eye suffering from dry eye are altered with lesser concentrations of proteins such as cytokine which promotes inflammation. Additionally, soluble mucin is greatly decreased due to loss of goblet cells which impacts viscosity of the tear film. Moreover, there is an increase in electrolyte concentration.

Throughout the world, countless individuals suffer from dry eye syndrome. The abnormalities leading to tear film dysfunction may be subdivided into four general categories: (a) aqueous tear deficiencies, which are most frequently responsible for dry eye states, originate from lacrimal gland disorders and include autoimmune disease, congenital alacrima, paralytic hyposecretion or excretory duct obstruction; (b) mucin deficiency, which is observed in various conjunctival cicatrization conditions, such as Stevens-Johnson syndrome, trachoma, pemphigoid, thermal and chemical burns, as well as hypovitaminosis A; (c) lipid abnormalities, which may occur during eyelid inflammation (e.g. chronic blepharitis); and (d) diminished eyelid function [Holly, F. J., Tear film physiology. Internat. Ophthalmol. Clin. 27:2-6 (1987)].

The first line of treatment is usually eye drops, preferably preservative free, that act as artificial tears. Most artificial tears are hydrogels that increase the moisture content on the eye surface and give some temporary relief. These solutions and ointments give some temporary relief, but do little to arrest or reverse any damaging conditions. A recently introduced artificial tear product is based on Castor oil emulsion (Refresh Endura tears).

In addition, warm moist compresses applied to the skin of the closed eyelids are also used to reduce tear loss due to evaporation.

For more severe cases of dry eye, in which the cornea is inflamed, anti-inflammatory agents, such as topical steroids (in eye drops) are sometimes prescribed. One example includes the combination of castor oil with cyclosporine (Restasis).

Oral medicine for dry eye is also available. For example, pilocarpine, the active ingredient in Salagen™ or cevimeline, the active ingredient in Evoxac™, are known to stimulate specific receptors in lacrimal gland and cause increased secretion of tears.

Other remedies include punctal plugs and punctal closure (which block the tears from flowing down the tear duct into the nose), and food supplements, such as the commercially available Flaxseed oil supplement (Omega-3 Supplement, TheraTears).

Adenosine receptors are classified into four major classes: A1, A2a, A2b and A3. A3 adenosine receptors belong to the family of the Gi-protein associated cell surface receptors. Receptor activation leads to its internalization and the subsequent inhibition of adenylyl cyclase activity, cAMP formation and protein kinase A (PKA) expression, resulting in the initiation of various signaling pathways. PKA contains a catalytic subunit PKAc which dissociates from the parent molecule upon activation with cAMP.

SUMMARY OF THE INVENTION

In accordance with a first aspect, the invention provides a method for treating dry eye condition in an individual comprising administrating to said individual an amount of $A_3$ adenosine receptor ($A_3AR$) agonist, the amount being effective to ameliorate dry eye symptoms.

According to one embodiment, the invention provides a method for treating dry eye syndrome in an individual, comprising administrating to said individual an $A_3$ adenosine receptor ($A_3AR$) agonist. According to another embodiment, the dry eye condition is Sjogren's syndrome (SS).

In accordance with a second aspect, the invention provides a pharmaceutical composition for treating dry eye conditions comprising as active ingredient an amount of $A_3AR$ agonist and a physiologically acceptable carrier, the amount of said $A_3AR$ agonist being effective to ameliorate said dry eye conditions.

In accordance with a third aspect, the present invention provides the use of an $A_3AR$ agonist for the preparation of a pharmaceutical composition for treating dry eye conditions.

DETAILED DESCRIPTION OF EXEMPLARY EMBODIMENTS

Dry eye conditions and syndromes encompass a constellation of diverse disease processes that produce objective clinical signs of keratoconjunctivitis sicca (KCS). The classic prototype of the dry eye syndrome is Sjogren's syndrome, but there are many other causes of KCS including cicatrising conjunctival diseases such as trachoma and pemphigoid, non-cicatrising syndromes causing specific dry eye findings, and atypical syndromes such as keratomalacia in which the eye is symptomatically and objectively dry but tear production is paradoxically normal.

The main symptom of dry eye is usually a scratchy or sandy feeling as if something is in the eye. Other symptoms may include stinging or burning of the eye; episodes of excess tearing that follow periods of very dry sensation; a stringy discharge from the eye; and pain and redness of the eye. Sometimes individuals with dry eye experience heaviness of the eyelids or blurred, changing, or decreased vision, although loss of vision is uncommon.

Some individuals with dry eye may have tears that run down their cheeks. This is because the eye may be producing less of the lipid and mucin layers of the tear film, which help keep tears in the eye. When this happens, tears do not stay in the eye long enough to thoroughly moisten it.

The present invention provides a method for treating dry eye conditions, preferably dry eye syndrome, comprising providing an individual exhibiting one or more dry eye symptoms and signs with an amount of $A_3$ adenosine receptor ($A_3AR$) agonist, the amount being effective to treat the dry eye condition.

As appreciated, while the invention is described in the following detailed description with reference to the above method, it is to be understood that also encompassed within the present invention are compositions comprising the $A_3AR$ agonist for use in said treatment.

In the context of the present invention the term "dry eye condition" denotes any condition or syndrome which results in the manifestation of dry eye symptoms. It includes an already existing condition as well as pseudo dry eye conditions, i.e. conditions high predisposition of developing dry eye syndromes. Dry eye syndrome may be as a result of another underlying condition causing dry eye, for example, Sjogren's syndrome, menopause or rheumatoid arthritis. Dry eye may also be a complication of inflammation, e.g. Blepharitis or of a foreign body in the eye. Yet dry eye may be a result of infection, or a side effect of medications, or exposure to toxins, chemicals, or other substances may cause a symptom or condition of dry eye. Dry eye conditions may be manifested by one or more ophthalmologic clinical symptoms as known in the art. Some non-limiting examples may include foreign body sensation, burning, itching, irritation, redness, eye pain, blurred vision, degraded vision and excessive tearing.

The term "dry eye symptoms" which may be used interchangeably with the term "dry eye signs" is used herein to denote any sensation or change in normal function or structure of the eye that is experienced by an individual. A non-limiting list of signs which may be perceived by a subject and be indicative of an dry eye syndrome includes, dry eye feeling, sandy eye feeling, scratchy eye feeling, burning eye, stinging or itching eye, excessive tearing, eye pain, redness of the eye, blurred vision, degraded vision.

The terms "treating" or "treatment", and the like are used herein to refer to obtaining a desired pharmacological and physiological effect. The effect may be prophylactic in terms of preventing or partially preventing a disease, symptom or condition of dry eye and/or may be therapeutic in terms of a partial or complete cure of a disease, condition, symptom or adverse effect attributed to dry eye syndrome. The term "treatment", as used herein, covers any treatment of a disease in a mammal, particularly a human, and includes: (a) preventing dry eye syndrome from occurring in an individual which may be predisposed to develop dry eye syndrome but has not yet been diagnosed as having it, i.e., causing the clinical symptoms of dry eye syndrome not to develop in a subject that may be predisposed to dry eye syndrome but does not yet experience or display symptoms of dry eye syndrome; (b) inhibiting dry eye syndrome, i.e., arresting or reducing the development of dry eye syndrome or its clinical symptoms; or (c) relieving dry eye syndrome, i.e., causing regression of dry eye syndrome and/or its symptoms or conditions.

The term "$A_3$ adenosine receptor agonist" ($A_3AR$ agonist) in the context of the present invention refers to any molecule capable of specifically binding to the $A_3AR$, thereby fully or partially activating said receptor. The $A_3AR$ agonist is thus a molecule that exerts its prime effect through the binding and activation of the $A_3AR$. This means that at the doses it is being administered it essentially binds to and activates only the $A_3AR$. In a preferred embodiment, an $A_3AR$ agonist has a binding affinity ($K_i$) to the human $A_3AR$ in the range of less than 100 nM, typically less than 50 nM, preferably less than 20 nM, more preferably less than 10 nM and ideally less than 5 nM. Particularly preferred are $A_3AR$ agonists that have a $K_i$ to the human $A_3R$ of less than 2 nM and desirably less than 1 nM.

It should be noted that some $A_3AR$ agonists can also interact with and activate other receptors with lower affinities (namely a higher Ki). A molecule will be considered an $A_3AR$ agonist in the context of the invention (namely a molecule that exerts its prime effect through the binding and activation $A_3AR$) if its affinity to the $A_3AR$ is at least 3 times (i.e. its Ki to the $A_3AR$ is at least 3 times lower), preferably 10 times, desirably 20 times and most preferably at least 50 times larger than the affinity to any other of the adenosine receptors (i.e. $A_1$, $A_{2a}$ and $A_{2b}$).

The affinity of an $A_3AR$ agonist to the human $A_3AR$ as well as its relative affinity to the other human adenosine receptors can be determined by a number of assays, such as a binding assay. Examples of binding assays include providing membranes containing a receptor and measuring the ability of the $A_3AR$ agonist to displace a bound radioactive agonist; utilizing cells that display the respective human adenosine receptor and measuring, in a functional assay, the ability of the $A_3AR$ agonist to activate or deactivate, as the case may be, downstream signaling events such as the effect on adenylate cyclase measured through increase or decrease of the cAMP level; etc. Clearly, if the administered level of an $A_3AR$ agonist is increased such that its blood level reaches a level approaching that of the Ki of the $A_1$, $A_{2a}$ and $A_{2b}$ adenosine receptors, activation of these receptors may occur following such administration, in addition to activation of the $A_3AR$. An $A_3AR$ agonist is thus preferably administered at a dose such that the blood level is such so that essentially only the $A_3AR$ will be activated.

The characteristic of some adenosine $A_3AR$ agonists and methods of their preparation are described in detail in, inter alia, U.S. Pat. No. 5,688,774; U.S. Pat. No. 5,773,423, U.S. Pat. No. 5,573,772, U.S. Pat. No. 5,443,836, U.S. Pat. No. 6,048,865, WO 95/02604, WO 99/20284, WO 99/06053, WO 97/27173 and applicant's co-pending patent application Ser. No. 09/700,751 (corresponding to WO 01/19360), all of which are incorporated herein by reference.

The following examples are specified in U.S. Pat. No. 5,688,774 at column 4, lines 67-column 6, line 16; column 5, lines 40-45; column 6, lines 21-42; column 7, lines 1-11; column 7, lines 34-36; and column 7, lines 60-61:

$N^6$-(3-iodobenzyl)-9-methyladenine;
$N^6$-(3-iodobenzyl)-9-hydroxyethyladenine;
R—$N^6$-(3-iodobenzyl)-9-(2,3-dihydroxypropyl)adenine;
S—$N^6$-(3-iodobenzyl)-9-(2,3-dihydroxypropyl)adenine;
$N^6$-(3-iodobenzyladenin-9-yl)acetic acid;
$N^6$-(3-iodobenzyl)-9-(3-cyanopropyl)adenine;
2-chloro-$N^6$-(3-iodobenzyl)-9-methyladenine;
2-amino-$N^6$-(3-iodobenzyl)-9-methyladenine;
2-hydrazido-$N^6$-(3-iodobenzyl)-9-methyladenine;

N⁶-(3-iodobenzyl)-2-methylamino-9-methyladenine;
2-dimethylamino-N⁶-(3-iodobenzyl)-9-methyladenine;
N⁶-(3-iodobenzyl)-9-methyl-2-propylaminoadenine;
2-hexylamino-N⁶-(3-iodobenzyl)-9-methyladenine;
N⁶-(3-iodobenzyl)-2-methoxy-9-methyladenine;
N⁶-(3-iodobenzyl)-9-methyl-2-methylthioadenine;
N⁶-(3-iodobenzyl)-9-methyl-2-(4-pyridylthio)adenine;
(1S, 2R, 3S, 4R)-4-(6-amino-2-phenylethylamino-9H-purin-9-yl)cyclopentane-1,2,3-triol;
(1S, 2R, 3S, 4R)-4-(6-amino-2-chloro-9H-purin-9-yl) cyclopentane-1,2,3-triol;
(±)-9-[2α,3α-dihydroxy-4β-(N-methylcarbamoyl)cyclopent-1β-yl)]-N⁶-(3-iodobenzyl)-adenine;
2-chloro-9-(2'-amino-2',3'-dideoxy-β-D-5'-methyl-arabinofuronamido)-N⁶-(3-iodobenzyl)adenine;
2-chloro-9-(2',3'-dideoxy-2'-fluoro-β-D-5'-methyl-arabino furonamido)-N⁶-(3-iodobenzyl)adenine;
9-(2-acetyl-3-deoxy-β-D-5-methyl-ribofuronamido)-2-chloro-N⁶-(3-iodobenzyl)adenine;
2-chloro-9-(3-deoxy-2-methanesulfonyl-β-D-5-methyl-ribofuronamido)-N⁶-(3-iodobenzyl)adenine;
2-chloro-9-(3-deoxy-β-D-5-methyl-ribofuronamido)-N⁶-(3-iodobenzyl)adenine;
2-chloro-9-(3,5-1,1,3,3-tetraisopropyldisiloxyl-β-D-5-ribofuranosyl)-N⁶-(3-iodobenzyl)adenine;
2-chloro-9-(2',3'-O-thiocarbonyl-β-D-5-methyl-ribofuronamido)-N⁶-(3-iodobenzyl)adenine;
9-(2-phenoxythiocarbonyl-3-deoxy-β-D-5-methyl-ribofuronamido)-2-chloro-N⁶-(3-iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido)-N⁶benzyladenine;
2-chloro-9-(2'-azido-2',3'-dideoxy-β-D-5'-methyl-arabinofuronamido)-N⁶-benzyladenine;
2-chloro-9-(β-D-erythrofuranoside)-N⁶-(3-iodobenzyl)adenine;
N⁶-(benzodioxanemethyl)adenosine;
1-(6-furfurylamino-9H-purin-9-yl)-1-deoxy-N-methyl-β-D-ribofuranosiduronamide;
N⁶-[3-(L-prolylamino)benzyl]adenosine-5'-N-methyluronamide;
N⁶-[3-(β-alanylamino)benzyl]adenosine-5'-N-methyluronamide;
N⁶-[3-(N-T-Boc-β-alanylamino)benzyl]adenosine-5'-N-methyluronamide
6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-N⁶-[(3-β-alanylamino)benzyl]adenosine;
9-(β-D-erythrofuranoside)-2-methylamino-N⁶-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine; and
2-chloro-(6'-thio-L-arabinosyl)adenine.

In U.S. Pat. No. 5,773,423 at column 6, line 39, to column 7, line 14, specifically disclosed are compounds which include the formula:

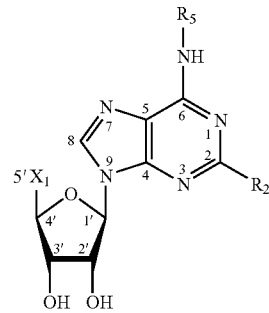

wherein $X_1$ is $R^a R^b NC(\!=\!O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_2$ is selected from the group consisting of hydrogen, halo, $C_1$-$C_{10}$ alkyoxy, amino, $C_2$-$C_{10}$ alkenyl, and $C_2$-$C_{10}$ alkynyl; and $R_5$ is selected from the group consisting of R- and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo.

More specific compounds include those of the above formula wherein $R^a$ and $R^b$ may be the same or different and are selected from the group consisting of hydrogen and $C_1$-$C_{10}$ alkyl, particularly when $R_2$ is hydrogen or halo, especially hydrogen.

Additional specific compounds are those compounds wherein $R^a$ is hydrogen and $R_2$ is hydrogen, particularly when $R_5$ is unsubstituted benzyl.

More specific compounds are such compounds wherein $R^b$ is a $C_1$-$C_{10}$ alkyl or $C_3$-$C_{10}$ cycloalkyl, particularly a $C_1$-$C_{10}$ alkyl, and more particularly methyl.

Especially specific are those compounds where $R^a$ is hydrogen, $R^b$ is $C_1$-$C_{10}$ alkyl or $C_3$-$C_{10}$ cycloalkyl, and $R_5$ is R- or S-1-phenylethyl or a benzyl substituted in one or more positions with a substituent selected from the group consisting of halo, amino, acetamido, $C_1$-$C_{10}$ haloalkyl, and sulfo, where the sulfo derivative is a salt, such as a triethylammonium salt.

An example of an especially preferred compound disclosed in U.S. Pat. No. 5,773,423 is IB-MECA. In addition, those compounds in which $R_2$ is a $C_2$-$C_{10}$ alkenylene of the formula $R^d$—C=C— where $R^d$ is a $C_1$-$C_8$ alkyl are particularly noted in this publication. Also specific are those compounds wherein $R_2$ is other than hydrogen, particularly those wherein $R_2$ is halo, $C_1$-$C_{10}$ alkylamino, or $C_1$-$C_{10}$ alkylthio, and, more preferably, when additionally $R^a$ is hydrogen, $R^b$ is a $C_1$-$C_{10}$ alkyl, and/or $R_5$ is a substituted benzyl.

Such specifically disclosed compounds include 2-chloro-N⁶-(3-iodobenzyl)-9-[5-(methylamido)-β-D-ribofuranosyl]-adenine, N⁶-(3-iodobenzyl)-2-methylamino-9-[5-(methylamido)-β-D-ribofuranosyl]-adenine, and N⁶-(3-iodobenzyl)-2-methylthio-9-[5-(methylamido)-β-D-ribofuranosyl]-adenine.

Further U.S. Pat. No. 5,773,423 discloses at column 7, line 60, through column 8, line 6, A₃AR agonists as modified xanthine-7-ribosides having the formula:

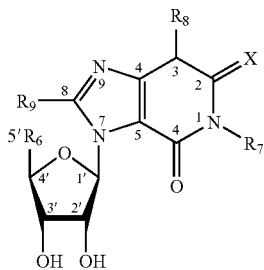

wherein

X is O;

$R_6$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_7$ and $R_8$ may be the same or different and are selected from the group consisting of $C_1$-$C_{10}$ alkyl, R- and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo; and $R_9$ is selected from the group consisting of halo, benzyl, phenyl, and $C_3$-$C_{10}$ cycloalkyl.

WO 99/06053 discloses in examples 19-33 compounds selected from:

$N^6$-(4-biphenyl-carbonylamino)-adenosine-5'-N-ethyluronamide;

$N^6$-(2,4-dichlorobenzyl-carbonylamino)-adenosine-5'-N-ethyluronamide;

$N^6$-(4-methoxyphenyl-carbonylamino)-adenosine-5'-N-ethyluronamide;

$N^6$-(4-chlorophenyl-carbonylamino)-adenosine-5'-N-ethyluronamide;

$N^6$-(phenyl-carbonylamino)-adenosine-5'-N-ethyluronamide;

$N^6$-(benzylcarbamoylamino)-adenosine-5'-N-ethyluronamide;

$N^6$-(4-sulfonamido-phenylcarbamoyl)-adenosine-5'-N-ethyluronamide;

$N^6$-(4-acetyl-phenylcarbamoyl)-adenosine-5'-N-ethyluronamide;

$N^6$-(4-α-phenylcarbamoyl)-adenosine-5'-N-ethyluronamide;

$N^6$-((R)-α-phenylethylcarbamoyl)-adenosine-5'-N-ethyluronamide;

$N^6$-((S)α-phenylethylcarbamoyl)-adenosine-5'-N-ethyluronamide;

$N^6$-(5-methyl-isoxazol-3-yl-carbamoyl)-adenosine-5'-N-ethyluronamide;

$N^6$-(1,3,4-thiadiazol-2-yl-carbamoyl)-adenosine-5'-N-ethyluronamide;

$N^6$-(4-n-propoxy-phenylcarbamoyl)-adenosine-5'-N-ethyluronamide;

$N^6$-bis-(4-nitrophenylcarbamoyl)-adenosine-5'-N-ethyluronamide; and $N^6$-bis-(5-chloro-pyridin-2-yl-carbamoyl)-adenosine-5'-N-ethyluronamide.

According to one embodiment of the invention, the $A_3AR$ agonist is a compound that exerts its prime effect through the binding and activation of the adenosine $A_3AR$ and is a purine derivative falling within the scope of the general formula (I):

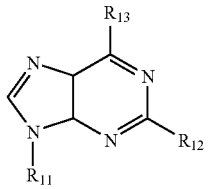

(I)

wherein, $R_{11}$ represents an alkyl, hydroxyalkyl, carboxyalkyl or cyanoalkyl or a group of the following general formula (II):

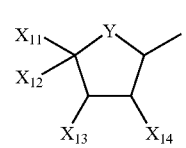

(II)

in which:

Y represents oxygen, sulfur or $CH_2$;

$X_{11}$ represents H, alkyl, $R^eR^fNC(=O)$— or $HOR^g$-, wherein $R^e$ and $R^f$ may be the same or different and are selected from the group consisting of hydrogen, alkyl, amino, haloalkyl, aminoalkyl, BOC-aminoalkyl, and cycloalkyl or are joined together to form a heterocyclic ring containing two to five carbon atoms; and $R^g$ is selected from the group consisting of alkyl, amino, haloalkyl, aminoalkyl, BOC-aminoalkyl, and cycloalkyl;

$X_{12}$ is H, hydroxyl, alkylamino, alkylamido or hydroxyalkyl;

$X_{13}$ and $X_{14}$ represent independently hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_{13}$ and $X_{14}$ are oxygens connected to >C=S to form a 5-membered ring, or $X_{12}$ and $X_{13}$ form the ring of formula (III):

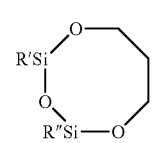

(III)

where R' and R" represent independently an alkyl group;

$R_{12}$ is selected from the group consisting of hydrogen, halo, alkylether, amino, hydrazido, alkylamino, alkoxy, thioalkoxy, pyridylthio, alkenyl; alkynyl, thio, and alkylthio; and $R_{13}$ is a group of the formula —$NR_{15}R_{16}$ wherein $R_{15}$ is a hydrogen atom or a group selected from alkyl, substituted alkyl or aryl-NH—C(Z)-, with Z being O, S, or $NR^a$ with $R^e$ having the above meanings; wherein when $R_{15}$ is hydrogen than $R_{16}$ is selected from the group consisting of R- and S-1-phenylethyl, benzyl, phenylethyl or anilide groups unsubstituted or substituted in one or more positions with a substituent selected from the group consisting of alkyl, amino, halo, haloalkyl, nitro, hydroxyl, acetoamido, alkoxy, and sulfonic acid or a salt thereof; benzodioxanemethyl, fururyl, L-propylalanyl-aminobenzyl, β-alanylamino-benzyl, T-BOC-β-alanylaminobenzyl, phenylamino, carbamoyl, phenoxy or cycloalkyl; or $R_{16}$ is a group of the following formula:

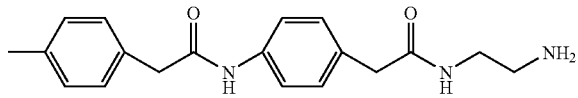

or when $R_{15}$ is an alkyl or aryl-NH—C(Z)-, then, $R_{16}$ is selected from the group consisting of heteroaryl-$NR^a$—C(Z)-, heteroaryl-C(Z)-, alkaryl-$NR^a$—C(Z)-, alkaryl-C(Z)-, aryl-NR—C(Z)- and aryl-C(Z)-; Z representing an oxygen, sulfor or amine; or a physiologically acceptable salt of the above compound.

According to one preferred embodiment, the $A_3AR$ agonist is a nucleoside derivative of the general formula (IV):

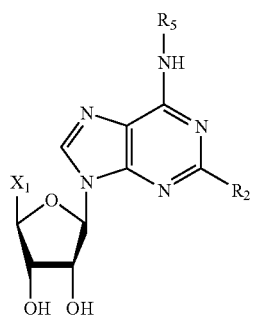

(IV)

wherein $X_1$, $R_2$ and $R_5$ are as defined above, and physiologically acceptable salts of said compound.

The non-cyclic carbohydrate groups (e.g. alkyl, alkenyl, alkynyl, alkoxy, aralkyl, alkaryl, alkylamine, etc) forming part of the substituent of the compounds of the present invention are either branched or unbranched, preferably containing from one or two to twelve carbon atoms.

When referring to "physiologically acceptable salts" of the compounds employed by the present invention it is meant any non-toxic alkali metal, alkaline earth metal, and ammonium salt commonly used in the pharmaceutical industry, including the sodium, potassium, lithium, calcium, magnesium, barium ammonium and protamine zinc salts, which are prepared by methods known in the art. The term also includes non-toxic acid addition salts, which are generally prepared by reacting the compounds of this invention with a suitable organic or inorganic acid. The acid addition salts are those which retain the biological effectiveness and qualitative properties of the free bases and which are not toxic or otherwise undesirable. Examples include, inter alia, acids derived from mineral acids, hydrochloric, hydrobromic, sulfuric, nitric, phosphoric, metaphosphoric and the like. Organic acids include, inter alia, tartaric, acetic, propionic, citric, malic, malonic, lactic, fumaric, benzoic, cinnamic, mandelic, glycolic, gluconic, pyruvic, succinic salicylic and arylsulphonic, e.g. p-toluenesulphonic, acids.

Specific examples of $A_3AR$ agonist which may be employed according to general formula (IV) of the present invention include, without being limited thereto, $N^6$-2-(4-aminophenyl)ethyladenosine (APNEA), $N^6$-(4-amino-3-iodobenzyl) adenosine-5'-(N-methyluronamide) (AB-MECA), $N^6$-(3-iodobenzyl)-adenosine-5'-N-methyluronamide (IB-MECA) and 2-chloro-$N^6$-(3-iodobenzyl)-adenosine-5'-N-methyluronamide (C1-IB-MECA). IB-MECA is the most preferred compound in accordance with the invention.

According to another embodiment, the $A_3AR$ agonist may be an oxide derivative of adenosine, such as $N^6$-benzyladenosine-5'-N-alkyluronamide-$N^1$-oxide or $N^6$-benzyladenosine-5'-N-dialkyluronamide-$N^1$-oxide, wherein the 2-purine position may be substituted with an alkoxy, amino, alkenyl, alkynyl or halogen.

The terms "effective amount" or "amount effective to" in the context of the present invention refer to an amount of $A_3AR$ agonist which prevents or reduces symptoms of dry eye in patients. The "effective amount" can be readily determined, in accordance with the invention, by administering to a plurality of tested subjects various amounts of the $A_3AR$ agonist and then plotting the physiological response (for example an integrated "SS index" combining several of the therapeutically beneficial effects) as a function of the amount. Alternatively, the effective amount may also be determined, at times, through experiments performed in appropriate animal models and then extrapolating to human beings using one of a plurality of conversion methods; or by measuring the plasma concentration or the area under the curve (AUC) of the plasma concentration over time and calculating the effective dose so as to yield a comparable plasma concentration or AUC. As known, the effective amount may depend on a variety of factors such as mode of administration (for example, oral administration may require a higher dose to achieve a given plasma level or AUC than an intravenous administration); the age, weight, body surface area, gender, health condition and genetic factors of the subject; other administered drugs; etc.

In the following, unless otherwise indicated, dosages are indicated in weight/Kg, meaning weight of administered $A_3AR$ agonist (e.g. IB-MECA) per kilogram of body weight of the treated subject in each administration. For example, mg/Kg and microgram/Kg denote, respectively, milligrams of administered agent and micrograms of administered agent per kilogram of body weight of the treated subject.

The effective amount is preferably less than about 1 mg/kg body weight, particularly less than about 500 μg/kg or even less than about 200 μg/kg body weight or at times less than about 100 μg/kg body weight or even less than about less than 50 μg/kg body weight. With respect to IB-MECA, the effective amount is preferably less than 5 mg each dose, for once daily administration (namely a dose less than about 70 μg/kg body weight, assuming an average individual weight of about 70 kg), and less than about 4 mg each dose (i.e. less than about 57 μg/kg body weight), for twice daily administration. The dose of IB-MECA is more preferably less than about 2 mg each dose and typically between about 0.1-1 mg each dose, for either once or twice daily administration (the corresponding dosages in weight per body weight being about 29 μg/kg and about 1.5-15 μg/kg body weight, respectively).

The administration of the $A_3AR$ agonist to an individual may be together with a pharmaceutically acceptable carrier. In the case where the administration is oral, the carrier is one that is acceptable for oral administration. In the case where the administration is topical, the carrier is one that is acceptable for topical administration, one example being ocular administration.

By the term "pharmaceutically acceptable carrier" it is meant any one of inert, non-toxic materials, which do not react with the $A_3AR$ agonist and which can be added to formulations as diluents or carriers or to give form or consistency to the formulation.

An oral formulation may be in the form of a pill, capsule, in the form of a syrup, an aromatic powder, and other various forms. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers may be any of those conventionally used and is limited only by chemical-physical considerations, such as solubility and lack of reactivity with the $A_3AR$ agonist, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way.

Typical examples of carriers suitable for oral administration comprise (a) liquid solutions, where an effective amount of the active substance is dissolved in diluents, such as water, saline, natural juices, alcohols, syrups, etc.; (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of the tragacanth as solids or granules; (c) powders; (d) suspensions in an appropriate liquid; (e) suitable emulsions; (f) liposome formulation; and others.

A topical formulation may be in any form suitable for topical administration, including, without being limited thereto, an ophthalmic solution (e.g. eye drops), an ophthalmic gel or an ophthalmic ointment or oily lotion. Topical administration of the $A_3AR$ agonist also comprises the use of ophthalmic patches carrying the $A_3AR$ agonist in a suitable drug containing layer and to be placed on top of the eyelid as well as to Ocular inserts which are devices containing the $A_3AR$ agonist and placed into the inferior or superior conjunctival sacs (see for example WO0059420).

Eye drops may be prepared by dissolving $A_3AR$ agonist in a sterile aqueous solution such as saline, buffering solution etc., or by combining powder compositions to be dissolved before use. Other additives may be included in the eye drops such as isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mahnitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, etc.).

Eye ointments may be prepared by mixing A3AR agonist into a base. Examples of the base for eye ointment include petrolatum, selen 50, Plastibase, macrogol, etc., but not limited thereto.

Some exemplary ophthalmic viscosity enhancers that can be used in the present formulation include: carboxymethyl cellulose sodium; methylcellulose; hydroxypropyl cellulose; hydroxypropylmethyl cellulose; hydroxyethyl cellulose; polyethylene glycol 300; polyethylene glycol 400; polyvinyl alcohol; and providone.

Some natural products, such as veegum, alginates, xanthan gum, gelatin, acacia and tragacanth, may also be used to increase the viscosity of ophthalmic solutions.

A tonicity is important because hypotonic eye drops cause an edema of the cornea, and hypertonic eye drops cause deformation of the cornea. The ideal tonicity is approximately 300 mOsM. The tonicity can be achieved by methods described in Remington: The Science and Practice of Pharmacy, known to those versed in the art.

As used herein, the forms "a", "an" and "the" include singular as well as plural references unless the context clearly dictates otherwise. For example, the term "an $A_3AR$ agonist" includes one or more compounds which are capable of specifically binding to the $A_3AR$, thereby fully or partially activating said receptor.

Further, as used herein, the term "comprising" is intended to mean that the composition include the recited active agent, i.e. $A_3AR$ agonist, but not excluding other elements, such as physiologically acceptable carriers and excipients as well as other active agents. The term "consisting essentially of" is used to define compositions which include the recited elements but exclude other elements that may have an essential significance on treatment of dry eye syndrome. "Consisting of" shall thus mean excluding more than trace elements of other elements. Embodiments defined by each of these transition terms are within the scope of this invention.

Further, all numerical values, e.g. when referring the amounts or ranges of the elements constituting the composition comprising the $A_3AR$ agonist as an active ingredient, are approximations which are varied (+) or (−) by up to 20%, at times by up to 10% of from the stated values. It is to be understood, even if not always explicitly stated that all numerical designations are preceded by the term "about".

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

SOME NON-LIMITING EXAMPLES

IB-MECA Improves Dry Eye Symptoms in Rheumatoid Arthritis Patients

Drug:

The $A_3AR$ agonist used was a clinical grade of the compound known generically as 1-Deoxy-1-[6-[[(3-iodophenyl)methyl]amino]-9H-purine-9-yl]-N-methyl-D-ribofuranuronamide or as $N^6$-(3-iodobenzyl)-adenosine-5'-N-methyluronamide (IB-MECA), that was synthesized for Can-Fite BioPharma, under good clinical practice (GMP) by Albany Molecular Research Inc, Albany, N.Y., USA.

The IB-MECA was formulated in oval softgel capsules. The capsules contained solutions of IB-MECA in Cremophor RH 40 and Miglyol 812. The capsules contained a dose of 0.1, 1 or 4 mg of IB-MECA, the exact composition of each capsules' type is shown in the following Tabels 1-3:

TABLE 1

Composition of 0.1 mg IB-MECA Softgel Capsules

| Ingredient | Capsule | % W/W |
| --- | --- | --- |
| IB-MECA | 0.105 mg | 0.021 |
| Polyoxyl 45 Castor Oil, USP (Cremophor RH 40) | 326.495 mg | 65.299 |
| Miglyol 812 | 173.400 mg | 34.680 |

TABLE 2

Composition of 1 mg IB-MECA Softgel Capsules

| Ingredient | Capsule | % W/W |
| --- | --- | --- |
| IB-MECA | 1.05 mg | 0.210 |
| Polyoxyl 45 Castor Oil, USP (Cremophor RH 40) | 325.975 mg | 65.195 |
| Miglyol 812 | 172.975 mg | 34.595 |

TABLE 3

Composition of 4 mg IB-MECA Softgel Capsules

| Ingredient | Capsule | % W/W |
| --- | --- | --- |
| IB-MECA | 4.2 mg | 0.84 |
| Polyoxyl 45 Castor Oil, USP (Cremophor RH 40) | 324.4 mg | 64.88 |
| Miglyol 812 | 171.4 mg | 34.28 |

Methods:

The capsules with IB-MECA were given to patients orally twice daily. All patients had rheumatoid arthritis (RA) and were give IB-MECA within the framework of a clinical study aimed at testing the effect of IB-MECA in modifying RA disease symptoms in these patients. The patients received randomly capsules of one of the above there doses. The patients received the IB-MECA for a period of 12 weeks.

4 out of the treated patients also suffered from Sicca and the effect of IB-MECA on their dry eye symptoms was examined as well.

Results

Table 4 summarizes the results of IB-MECA treatment of RA patients. Specifically, four patients at the age 58±4 years who suffered from RA for 8±2 years were followed. At base line, the patients had elevated levels of rheumatoid factor, i.e., 313±120 IU/ml (0<normal<40) and had suffered from dry eyes for 5±1.6 years. Upon treatment with IB-MECA for 6.25±1.1 months, an improvement in Schirmer's test from 8.5±1.4 mm to 15.6±2.9 mm was observed.

TABLE 4

Effect of IB-MECA treatment (twice daily) on RA patients

| | | | | | | | Schirmer test | | | |
| --- | --- | --- | --- | --- | --- | --- | --- | --- | --- | --- |
| | | | RA | Dry eye | | Period of | Left eye | | Right eye | |
| Patient | Dose | Age (years) | duration (years) | duration (years) | Hepatitis C Virus | treatment (month) | Base line | End of study | Base line | End of study |
| 1 | 0.1 | 65 | 14 | 5 | positive | 4 | 6 | 9 | 14 | 9 |
| 2 | 1.0 | 58 | 7 | 7 | positive | 5 | 10 | 32 | 15 | 23 |
| 3 | 4.0 | 54 | 6 | 5 | | 7 | 5 | 16 | 5 | 17 |
| 4 | 1.0 | 70 | 5 | 3 | | 9 | 6 | 9 | 7 | 10 |
| Mean | | 61.75 | 8.00 | 5 | | 6.25 | 6.75 | 16.5 | 10.25 | 14.75 |
| SE | | 2.4 | 0.51 | 0.82 | | 1.11 | 1.11 | 5.4 | 2.5 | 3.28 |

Treatment of Secondary Sjogren Syndrome Symptoms in Rheumatoid Arthritis Patients A patient with rheumatoid arthritis (RA) and secondary Sjogren symptoms, mainly manifested by dry eye, treated for years with eye drops (tear substitutes) participated in a phase 2 clinical trial with IB-MECA for the treatment of active RA. The patient's symptoms of dry eye were improved significantly, to the extent of discontinuation of the use of tear substitutes.

Methods

The patient took part in a phase 2, multicenter, randomized, double-blind, parallel-group, dose-ranging study of the safety and preliminary efficacy of daily IB-MECA administered orally for 12 weeks to patients with active rheumatoid arthritis.

The patient is a 53 years old female with a 7 year history of RA, previously treated with 3 disease-modifying anti-rheumatic drugs (DMARDs), and a history of 2-3 years of dry eyes treated with tear substitutes a few times a day. After a 4 week DMARD washout period, the patient was treated with a blinded dose of IB-MECA—either 0.1, 1.0 or 4.0 mg q 12 h for 12 weeks. She is currently continuing IB-MECA treatment under a long term extension protocol of the original 12 weeks study.

Results

There had been a marked improvement in the condition of the RA in this patient, represented by objective measurements of swollen and tender joints, acute phase reactants (ESR and CRP), patient and physician global assessments, patient assessment of pain and disability. Although the evaluation of secondary Sjogren's symptoms had not been a part of the patient evaluation in this study, the patient reported that after years of continuous use of tear substitutes for dry eye, after about 3-4 weeks of IB-MECA administration she did not need them any more, and she currently has no symptoms of dry eye.

CONCLUSION

Treatment with IB-MECA resulted in a substantial improvement of the dry eye symptoms of secondary Sjogren's syndrome in a patient with active RA

The invention claimed is:

1. A method for treating a dry eye condition in an individual comprising administrating to said individual an amount of $A_3$ adenosine receptor ($A_3AR$) agonist, the amount being effective to ameliorate symptoms of dry eye in the individual, wherein the $A_3AR$ agonist is a compound of the general formula (I):

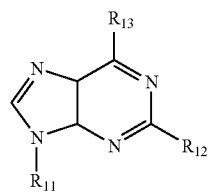

(I)

or of general formula (I')

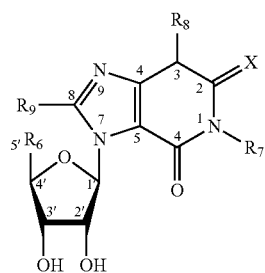

(I')

wherein in formula (I), $R_{11}$ represents an alkyl, hydroxyalkyl, carboxylalkyl or cyanoalkyl or a group of the following general formula (II):

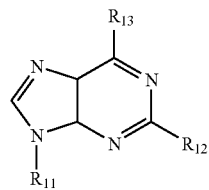

(I)

in which

Y represents oxygen, sulfur or CH2;

$X_{11}$ represents H, alkyl, $R^eR^fNC(=O)$-or $HOR^g$-, wherein $R^e$ and $R^f$ may be the same or different and are selected from the group consisting of hydrogen, alkyl, amino, haloalkyl, aminoalkyl, BOC-aminoalkyl, and cycloalkyl; or are joined together to form a heterocyclic ring containing two to five carbon atoms; and $R^g$ is selected from the group consisting of alkyl, amino, haloalkyl, aminoalkyl, BOC-aminoalkyl, and cycloalkyl;

$X_{12}$ is H, hydroxyl, alkylamino, alkylamido orhydroxyalkyl;

$X_{13}$ and $X_{14}$ represent independently hydrogen, hydroxyl, amino, amido, azido, halo, alkyl, alkoxy, carboxy, nitrilo, nitro, trifluoro, aryl, alkaryl, thio, thioester, thioether, -OCOPh, -OC(=S)OPh; or both $X_{13}$ and $X_{14}$ are oxygens connected to >C=S to form a 5-membered ring, or $X_{12}$ and $X_{13}$ form a ring of the following formula (III):

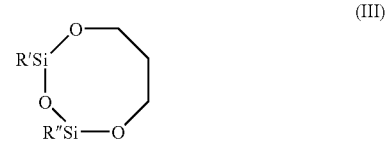

(III)

where R' and R" represent independently an alkyl group;

$R_{12}$ is selected from the group consisting of hydrogen, halo, alkylether, amino, hydrazido, alkylamino, alkoxy, thioalkoxy, pyridylthio, alkenyl; alkynyl, thio, and alkylthio; and $R_{13}$ is a group of the formula -$NR_{15}R_{16}$ wherein $R_{15}$ is a hydrogen atom or a group selected from alkyl, substituted alkyl or aryl-NH—C(Z)-, with Z being O, S, or $NR^a$ with $R^e$ having the above meanings; wherein when $R_{15}$ is hydrogen then $R_{16}$ is selected from the group consisting of R-and S-1-phenylethyl, benzyl, phenylethyl or anilide groups unsubstituted or substituted in one or more positions with a substituent selected from the group consisting of alkyl, amino, halo, haloalkyl, nitro, hydroxyl, acetoamido, alkoxy, and sulfonic acid or a salt thereof; benzodioxanemethyl, fururyl, L-propylalanyl-aminobenzyl, β-alanylamino-benzyl,T-BOC-β-alanylaminobenzyl, phenylamino, carbamoyl, phenoxy or cycloalkyl; or $R_{16}$ is a group of the following formula

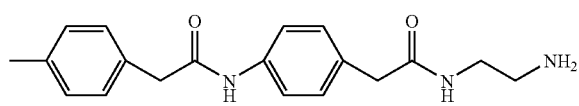

or when $R_{15}$ is an alkyl or aryl-NH—C(Z)-, then $R_{16}$ is selected from the group consisting of heteroaryl-$NR^a$—C(Z)-, heteroaryl-C(Z)-, alkaryl-$NR^a$—C(Z)-, alkaryl-, C(Z)-, aryl-NR—C(Z)-and aryl-C(Z)-; Z representing an oxygen, sulfur or amine;

and in formula (I')

X is O;

$R_6$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_7$ and $R_8$ may be the same or different and are selected from the group consisting of $C_1$-$C_{10}$ alkyl, R-and S-1-phenylethyl, an unsubstituted benzyl group, and a benzyl group substituted in one or more positions with a substituent selected from the group consisting of $C_1$-$C_{10}$ alkyl, amino, halo, C $C_1$-$C_{10}$ haloalkyl, nitro, hydroxy, acetamido, $C_1$-$C_{10}$ alkoxy, and sulfo; and $R_9$ is selected from the group consisting of halo, benzyl, phenyl, and $C_3$-$C_{10}$ cycloalkl or any physiologically acceptable salt thereof.

2. The method of claim 1, wherein the $A_3AR$ agonist is a compound of general formula (IV):

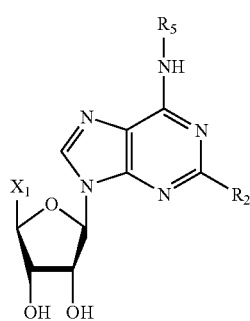

wherein $X_1$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_2$ is selected from the group consisting of hydrogen, halo, $C_1$-$C_{10}$ alkyoxy, amino, $C_2$-$C_{10}$ alkenyl, and $C_2$-$C_{10}$ alkynyl; and $R_5$ is selected from the group consisting of R-and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo; or any pharmaceutically acceptable salt thereof.

3. The method according to claim 1, wherein the $A_3AR$ agonist is selected from the group consisting of:

$N^6$-(3-iodobenzyl)-9-methyladenine;
$N^6$-(3-iodobenzyl)-9-hyd roxyethyladenine;
R—$N^6$-(3-iodobenzyl)-9-(2,3-dihydroxypropyl)adenine;
S—$N^6$-(3-iodobenzyl)-9-(2,3-dihydroxypropyl)adenine;
$N^6$-(3-iodobenzyladenin-9-yl)acetic acid;
$N^6$-(3-iodobenzyl)-9-(3-cyanopropyl)adenine;
2-chloro-$N^6$-(3-iodobenzyl)-9-methyladenine;
2-amino-$N^6$-(3-iodobenzyl)-9-methyladenine;
2-hydrazido-$N^6$-(3-iodobenzyl)-9-methyladenine;
$N^6$-(3-iodobenzyl)-2-methylamino-9-methyladenine;
2-dimethylamino-$N^6$-(3-iodobenzyl)-9-methyladenine;
$N^6$-(3-iodobenzyl)-9-methyl-2-propylaminoadenine;
2-hexylamino-$N^6$-(3-iodobenzyl)-9-methyladenine;
$N^6$-(3-iodobenzyl)-2-methoxy-9-methyladenine;
$N^6$-(3-iodobenzyl)-9-methyl-2-methylthioadenine;
$N^6$-(3-iodobenzyl)-9-methyl-2-(4-pyridylthio)adenine;
(1S, 2R, 3S, 4R)-4-(6-amino-2-phenylethylamino-9H-purin-9-yl)cyclopentane-1,2,-3-triol;
(1S, 2R, 3S, 4R)-4-(6-amino-2-chloro-9H-purin-9-yl)cyclopentane-1,2,3-triol;
(±)-9-[2α,3 α-dihydroxy-4β-(N-methylcarbamoyl)cyclopent-1β-yl)]-$N^6$-(3-iodobenzyl)-adenine;
2-chloro-9-(2'-amino-2 ', 3'-dideoxy-β-D-5'-methyl-arabino-furonamido)-$N^6$-(3-iodobenzyl)adenine;
2-chloro-9-(2', 3'-dideoxy-2'-fluoro-β-D-5'-methyl-arabino furonamido)-$N^6$-(3-iodobenzyl)adenine;
9-(2-acetyl-3-deoxy-β-D-5-methyl-ribofuronamido)-2-chloro-$N^6$-(3-iodobenzyl)adenine;
2-chloro-9-(3-deoxy-2-methanesulfonyl-β-D-5-methyl-ribofuronamido)-$N^6$-(3-iodobenzyl)adenine;
2-chloro-9-(3-deoxy-β-D-5-methyl-ribofuronamido)-$N^6$-(3-iodobenzyl)adenine;
2-chloro-9-(3,5-1,1,3,3-tetraisopropyldisiloxyl-β-D-5-ribofuranosyl)-$N^6$-(3-iodobenzyl)adenine;
2-chloro-9-(2',3'-O-thiocarbonyl-β-D-5-methyl-ribofuronamido)-$N^6$-(3-iodobenzyl)adenine;
9-(2-phenoxythiocarbonyl-3-deoxy-β-D-5-methyl-ribofuronamido)-2-chloro-$N^6$-(3-iodobenzyl)adenine;
1-(6-benzylamino-9H-purin-9-yl)-1-deoxy-N,4-dimethyl-β-D-ribofuranos -iduronamide;
2-chloro-9-(2,3-dideoxy-β-D-5-methyl-ribofuronamido)-$N^6$benzyladenine;
2-chloro-9-(2'-azido-2',3'-dideoxy-β-D-5'-methyl-arabino-furonamido)-$N^6$-benzyladenine;
2-chloro-9-(β-D-erythrofuranoside)-$N^6$-(3-iodobenzyl)adenine;
$N^6$-(benzodioxanemethyl)adenosine;
1-(6-furfurylamino-9H-purin-9-yl)-1-deoxy-N-methyl β-D-ribofuranosiduronamide;
$N^6$-[3-(L-prolylamino)benzyl]adenosine-5'-N-methyluronamide;
$N^6$-[3-(β-alanylamino)benzyl]adenosine-5'-N-methyluronamide;
$N^6$-[3-(N-T-Boc-β-alanylamino)benzyl]adenosine-5'-N-methyluronamide 6-(N'-phenylhydrazinyl)purine-9β-ribofuranoside-5'-N-methyluronamide;
6-(O-phenylhydroxylamino)purine-9-β-ribofuranoside-5'-N-methyluronamide; 9-(β-D-2',3'-dideoxyerythrofuranosyl)-$N^6$-[(3 β-alanylamino)benzyl]adenosine;
9-(β-D-erythrofuranoside)-2-methylamino-$N^6$-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine;
2-chloro-(6'-thio-L-arabinosyl)adenine;
$N^6$-(4-biphenyl-carbonylamino)-adenosine-5'-N-ethyluronamide;
$N^6$-(2,4-dichlorobenzyl-carbonylamino)-adenosine-5'-N-ethyluronamide;
$N^6$-(4-methoxyphenyl-carbonylamino)-adenosine-5'-N-ethyluronamide;
$N^6$-(4-chlorophenyl-carbonylamino)-adenosine-5'-N-ethyluronamide;
$N^6$-(phenyl-carbonylamino)-adenosine-5'-N-ethyluronamide;
$N^6$-(benzylcarbamoylamino)-adenosine-5'-N-ethyluronamide;
$N^6$-(4-sulfonamido-phenylcarbamoyl)-adenosine-5'-N-ethyluronamide;
$N^6$-(4-acetyl-phenylcarbamoyl)-adenosine-5'-N-ethyluronamide;
$N^6$-(4-α-phenylcarbamoyl)-adenosine-5'-N-ethyluronamide;
$N^6$-((R)-α-phenylethylcarbamoyl)-adenosine-5'-N-ethyluronamide;
$N^6$-((S)-α-phenylethylcarbamoyl)-adenosine-5'-N-ethyluronamide;
$N^6$-(5-methyl-isoxazol-3-yl-carbamoyl)-adenosine-5'-N-ethyluronamide;
$N^6$-(1,3,4-thiadiazol-2-yl-carbamoyl)-adenosine-5'-N-ethyluronamide;
$N^6$-(4-n-propoxy-phenylcarbamoyl)-adenosine-5'-N-ethyluronamide;
$N^6$-bis-(4-nitrophenylcarbamoyl)-adenosine-5'-N-ethyluronamide;
$N^6$-bis-(5-chloro-pyridin-2-yl-carbamoyl)-adenosine-5'-N-ethyluronamide; and
any pharmaceutically acceptable salt thereof.

4. The method of claim 1, wherein the dry eye condition is a dry eye syndrome.

5. The method of claim 1, wherein the dry eye condition is secondary Sjögren's syndrome.

6. The method of claim 1, wherein the $A_3AR$ agonist is orally administered.

7. The method of claim 6, wherein the $A_3AR$ agonist is administered twice a day.

8. The method of claim 1, wherein the $A_3AR$ agonist is administered topically to the individual.

9. The method of claim 6, wherein the $A_3AR$ agonist is administered to the eye.

10. The method of claim 1, wherein the $A_3AR$ agonist is selected from the group consisting of $N^6$-2-(4-aminophenyl) ethyladenosine (APNEA), $N^6$-(4-amino -3-iodobenzyl) adenosine-5'-(N-methyluronamide)(AB-MECA), $N^6$-(3-iodobenzyl) -adenosine-5'-N-methyluronamide (IB-MECA) and 2-chloro-$N^6$-(3-iodobenzyl)-adenosine -5'-N-methyluronamide (CI-IB-MECA).

11. The method of claim 10, wherein the $A_3AR$ agonist is IB -MECA.

12. The method of claim 1, wherein the dry eye condition is manifested by one or more ophthalmologic clinical symptoms selected from the group consisting of foreign body sensation, burning, itching, irritation, redness, eye pain, blurred vision, degraded vision and excessive tearing.

13. The method of claim 1, wherein the $A_3AR$ agonist has a binding affinity ($K_i$) to the human $A_3AR$ of less than 100 nM.

14. The method of claim 1, wherein the $A_3AR$ agonist has a binding affinity ($K_i$) to the human $A_3AR$ of less than 50 nM.

15. The method of claim 1, wherein the $A_3AR$ agonist has a binding affinity ($K_i$) to the human $A_3AR$ of less than 20 nM.

* * * * *